US00PP32552P2

(12) United States Plant Patent
van den Hoogen

(10) Patent No.: US PP32,552 P2
(45) Date of Patent: Dec. 1, 2020

(54) ***VERONICA* PLANT NAMED 'ALLARTIST'**

(50) Latin Name: ***Veronica longifolia* x *Veronica spicata***
Varietal Denomination: Allartist

(71) Applicant: Wilhelmus T. J. van den Hoogen, Cuijk (NL)

(72) Inventor: Wilhelmus T. J. van den Hoogen, Cuijk (NL)

(73) Assignee: ALL PLANTS HOLDING B.V., Cuijk (NL)

( * ) Notice: Subject to any disclaimer, the term of this patent is extended or adjusted under 35 U.S.C. 154(b) by 0 days.

(21) Appl. No.: 16/602,800

(22) Filed: Dec. 3, 2019

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./226, 251
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Veronica* plant named 'Allartist', characterized by its upright plant habit; dark green-colored leaves; freely flowering habit; dense inflorescences with numerous red purple-colored flowers; flowers are initially lighter red purple becoming darker red purple with development giving a two-tone appearance to the inflorescence; and good performance as a garden plant and as a cut flower.

2 Drawing Sheets

Figure 1:
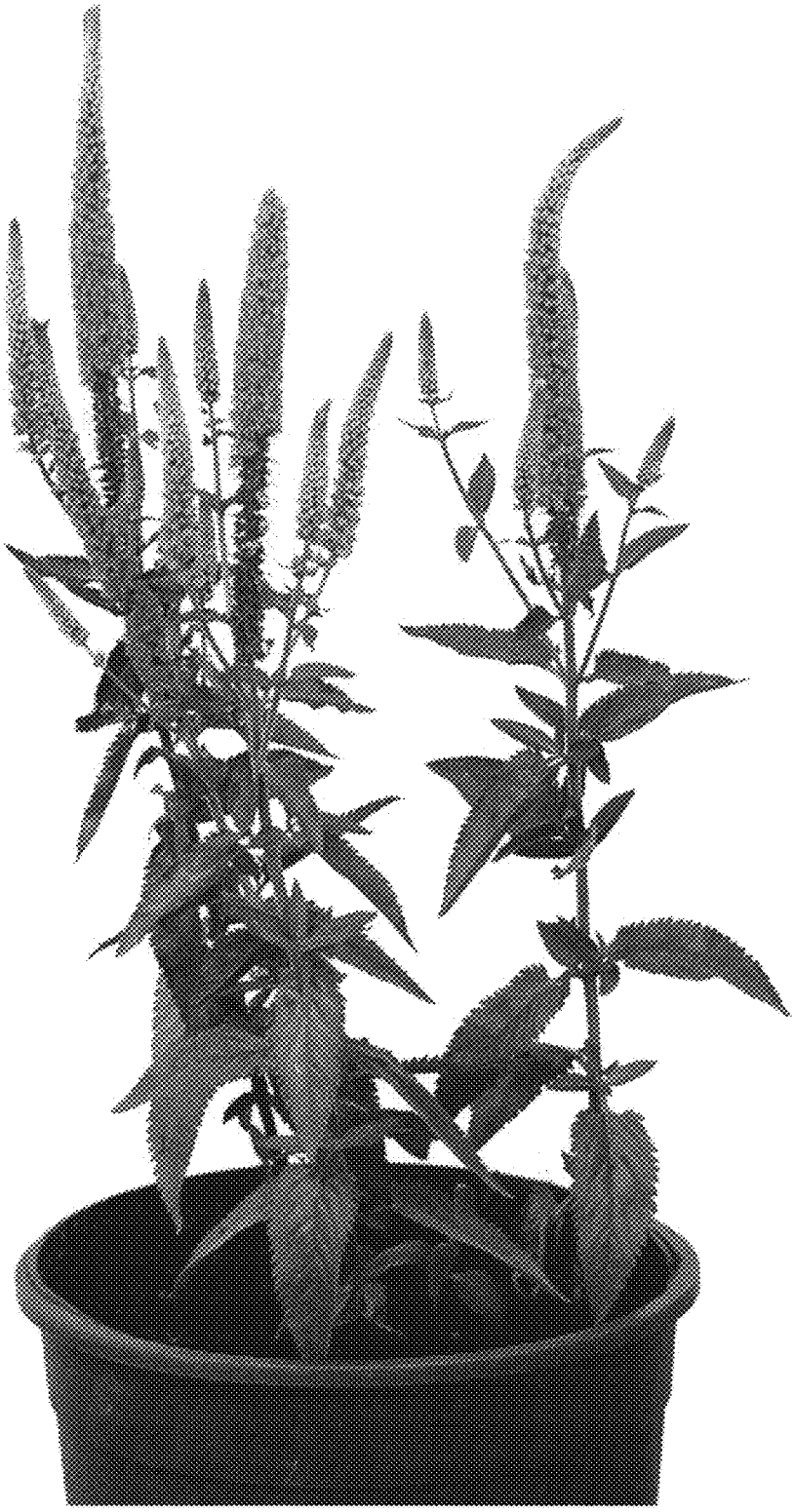

Botanical designation: *Veronica longifolia* x *Veronica spicata.*

Cultivar denomination: 'ALLARTIST'.

BACKGROUND OF THE INVENTION

The present invention relates to a new and distinct cultivar of *Veronica* plant, botanically known as *Veronica longifolia* x *Veronica spicata*, typically grown as a cut flower and hereinafter referred to by the name 'Allartist'.

The new *Veronica* plant is a product of a planned breeding program conducted by the Inventor in Cuijk, The Netherlands. The objective of the breeding program is to create new attractive *Veronica* plants with unique inflorescence form and color.

The new *Veronica* plant originated from an open-pollination in July, 2013 of a proprietary selection of *Veronica longifolia* x *Veronica spicata* identified as code number 13-74-8, not patented, as the female, or seed, parent with an unknown selection of *Veronica longifolia* x *Veronica spicata* as the male, or pollen, parent. The new *Veronica* plant was discovered and selected by the Inventor as a single flowering plant from within the progeny of the stated open-pollination in a controlled nursery environment in Cuijk, The Netherlands in August, 2014.

Asexual reproduction of the new *Veronica* plant by terminal stem cuttings in a controlled environment in Cuijk, The Netherlands, since September, 2014 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allartist'. These characteristics in combination distinguish 'Allartist' as a new and distinct *Veronica* plant:

1. Upright plant habit.
2. Dark green-colored leaves.
3. Freely flowering habit.
4. Dense inflorescences with numerous red purple-colored flowers; flowers are initially lighter red purple becoming darker red purple with development giving a two-tone appearance to the inflorescence.
5. Good performance as a garden plant and as a cut flower.

Plants of the new *Veronica* differ primarily from plants of the female parent selection in the following characteristics:

1. Plants of the new *Veronica* have fewer lateral branches than plants of the female parent selection.
2. Inflorescences of plants of the new *Veronica* are longer than inflorescences of plants of the female parent selection.
3. Flowers of plants of the new *Veronica* are darker red purple than flowers of plants of the female parent selection.

Plants of the new *Veronica* can be compared to plants of *Veronica longifolia* x *Veronica spicata* 'Alliselle', not patented. In side-by-side comparisons, plants of the new *Veronica* differ primarily from plants of 'Alliselle' in the following characteristics:

1. Inflorescences of plants of the new *Veronica* do not express any deformities whereas inflorescences ofplants of 'Alliselle' are slightly deformed.
2. Flowers of plants of the new *Veronica* are red purple in color whereas flowers of plants of 'Alliselle' are purple in color.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet (FIG. 1 of 2) comprises a side perspective view of a typical flowering plant of 'Allartist' grown in a container.

Figure 2:
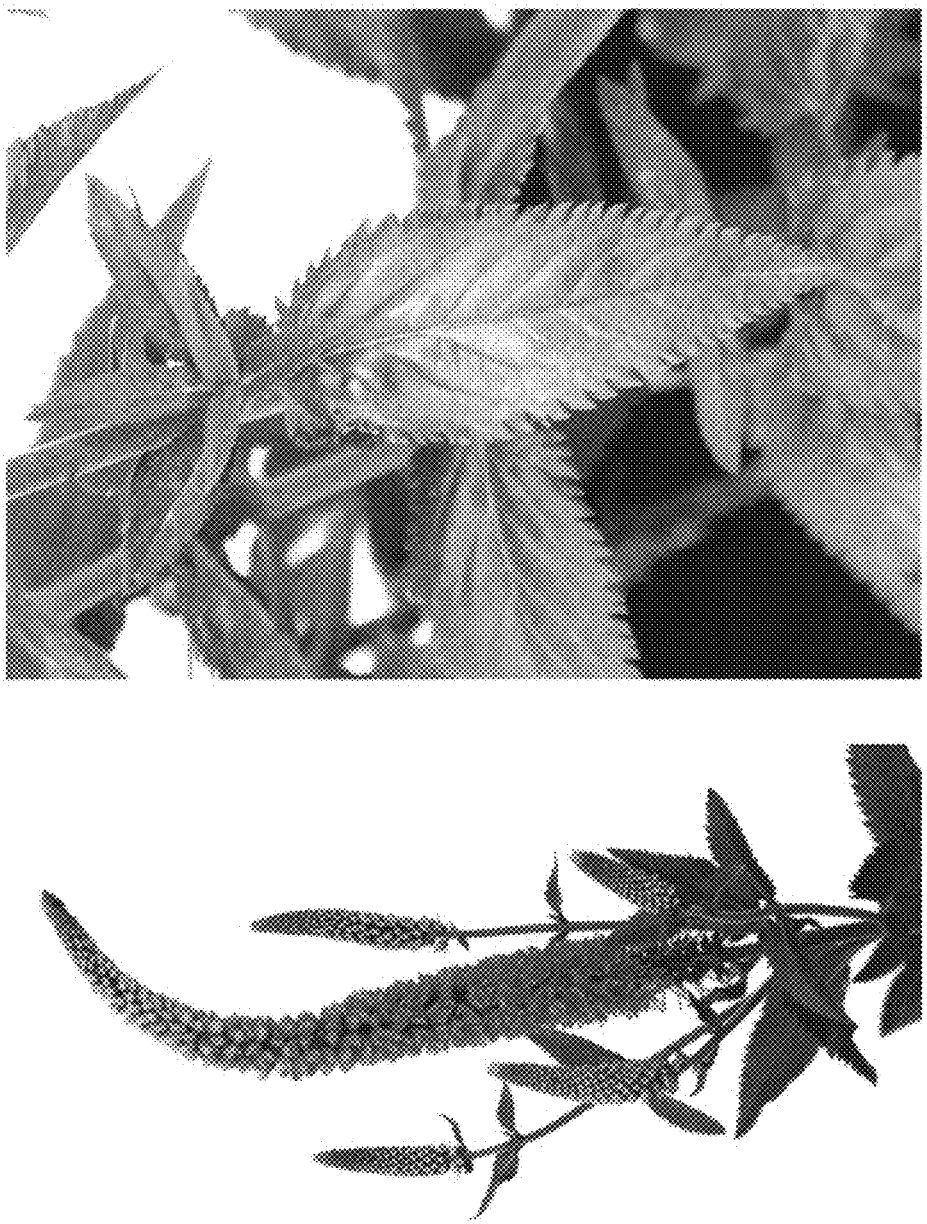

The photographs on the second sheet (FIG. 2 of 2) are close-up views of typical stems and leaves of 'Allartist' (upper photograph) and typical inflorescences of 'Allartist' (lower photograph).

DETAILED BOTANICAL DESCRIPTION

Plants used for the aforementioned photographs and following description were grown in 21-cm containers during the summer in an outdoor nursery in Cuijk, The Netherlands and under cultural practices typical of commercial *Veronica* production. During the production of the plants, day temperatures ranged from 12° C. to 24° C. and night temperatures ranged from 4° C. to 14° C. Plants were four months old when the photographs and the description were taken. In the following description, color references are made to The Royal Horticultural Society Colour Chart, 2015 Edition, except where general terms of ordinary dictionary significance are used.

Botanical classification: *Veronica longifolia* x *Veronica spicata* 'Allartist'.

Parentage:

*Female, or seed, parent.*—Proprietary selection of *Veronica longifolia* x *Veronica spicata* identified as code number 13-74-8, not patented.

*Male, or pollen, parent.*—Unknown selection of *Veronica longifolia* x *Veronica spicata*, not patented.

Propagation:

*Type cutting.*—Terminal stem cuttings.

*Time to initiate roots, summer.*—About 10 to 14 days at temperatures ranging from 12° C. to 30° C.

*Time to produce a rooted young plant, summer.*—About 24 to 32 days at temperatures ranging from 12° C. to 30° C.

*Root description.*—Fine, fleshy; typically white in color, actual color of the roots is dependent on substrate composition, water quality, fertilizer type and formulation, substrate temperature and physiological age of roots.

*Rooting habit.*—Freely branching; dense.

Plant description:

*Plant type.*—Herbaceous perennial.

*Plant and growth habit.*—Upright plant habit; overall plant shape, broadly oblong; moderately vigorous growth habit and moderate growth rate.

*Plant height, soil level to top of foliar plane.*—About 37.2 cm.

*Plant height, soil level to top of floral plane.*—About 50 cm.

*Plant width.*—About 25 cm.

*Lateral branch description.*—Branching habit: Freely branching habit with about four main stems; pinching will enhance lateral branching. Length: About 25.9 cm. Diameter: About 4 mm. Internode length: About 4 cm. Strength: Strong. Aspect: About 7.5° from vertical. Texture and luster: Densely pubescent; slightly glossy. Color, developing: Close to 144B. Color, developed: Close to 144A to 144B.

Leaf description:

*Arrangement.*—Opposite or in whorls of three, simple.

*Length.*—About 7.2 cm.

*Width.*—About 2.9 cm.

*Shape.*—Narrowly ovate to lanceolate; flat to slightly curled downward, very slightly carinate.

*Apex.*—Acute.

*Base.*—Truncate.

*Margin.*—Serrate.

*Texture and luster, upper surface.*—Moderately to densely pubescent; not rugose; slightly glossy.

*Texture and luster, lower surface.*—Moderately to densely pubescent; not rugose; matte.

*Venation pattern.*—Pinnate.

*Color.*—Developing leaves, upper surface: Close to 137A. Developing leaves, lower surface: Close to 146A. Fully expanded leaves, upper surface: Close to between NN137A and 147A; venation, close to 144A. Fully expanded leaves, lower surface: Close to between 147B and 191A; venation, close to 146B.

*Petioles.*—Length: About 1 cm. Diameter: About 2 mm by 3 mm. Strength: Strong. Texture and luster, upper and lower surfaces: Densely pubescent; slightly glossy. Color, upper surface: Close to 144B. Color, lower surface: Close to 144A.

Flower description:

*Flower arrangement and shape.*—Single campanulate flowers arranged on dense terminal compound racemes; flowers face mostly outwardly.

*Flowering habit.*—Freely flowering habit with about 1,600 flowers developing per inflorescence.

*Fragrance.*—None detected.

*Natural flowering season.*—Long flowering period; plants flower continuously from the summer until the autumn in The Netherlands.

*Flower longevity.*—Inflorescences last about 30 days on the plant and about 10 days as a cut flower; flowers not persistent.

*Flower buds.*—Length: About 4.5 mm. Diameter: About 2 mm. Shape: Obovate. Texture and luster: Smooth, glabrous; matte. Color: Close to 64C; developing calyx, close to 137C.

*Inflorescence height.*—About 19.8 cm.

*Inflorescence diameter.*—About 9 cm.

*Flower diameter.*—About 7 mm by 7 mm.

*Flower height.*—About 8.5 mm.

*Throat diameter.*—About 3 mm.

*Tube length.*—About 2 mm.

*Tube diameter.*—About 3 mm.

*Petals.*—Quantity and arrangement: Four in a single whorl; upper petal slightly larger than the lateral and lower petals; petals fused about 40% of the petal length from the base. Length, all petals: About 5 mm. Width, upper petal: About 4 mm. Width, lateral and lower petals: About 3 mm. Shape, upper petal: Obovate; moderately concave. Shape, lateral and lower petals: Oblong; moderately concave. Apex, all petals: Obtuse. Margin, all petals: Entire. Texture and luster, all petals, upper and lower surfaces: Smooth, glabrous; matte. Texture and luster, throat:

Smooth, glabrous; matte. Texture and luster, tube: Densely pubescent; matte. Color, all petals: When opening, upper and lower surfaces: Close to 64C. Fully opened, upper and lower surfaces: Close to 71C; color becoming closer to 71D with development. Throat: Close to 71C. Tube: Close to 71C and proximally, close to 155A.

*Sepals.*—Quantity and arrangement: Four arranged in a single whorl, fused at the base. Length: About 2 mm to 3 mm. Width: About 1 mm. Shape: Ovate. Apex: Acute. Base: Broadly cuneate, fused. Margin: Entire. Texture and luster, upper surface: Smooth, glabrous; matte. Texture and luster, lower surface: Moderately pubescent; matte. Color: When opening, upper surface: Close to 137C to 137D. When opening, lower surface: Close to 137C. Fully opened, upper and lower surfaces: Close to NN137C.

*Peduncles.*—Length, terminal peduncles: About 19.5 cm. Length, axillary peduncles: About 13.7 cm. Diameter, terminal and axillary peduncles: About 3 mm. Aspect, terminal peduncles: Upright. Aspect, axillary peduncles: About 25° from terminal peduncle axis. Strength, terminal and axillary peduncles: Strong. Texture and luster, terminal and axillary peduncles: Densely pubescent; slightly glossy. Color, terminal and axillary peduncles: Close to 144A.

*Pedicels.*—Length: About 1 mm. Diameter: About 0.5 mm. Aspect: About 60° from peduncle axis. Strength: Moderately strong. Texture and luster: Sparsely pubescent; slightly glossy. Color: Close to 143B.

*Reproductive organs.*—Stamens: Quantity per flower: Typically not observed, if present, one. Filament length: About 5 mm. Filament color: Close to 71C. Anther shape: Short oblong; dorsifixed. Anther size: About 1 mm by 0.5 mm. Anther color: Close to N92A. Pollen amount: Moderate. Pollen color: Close to 157A.

*Pistils.*—Quantity per flower: One. Pistil length: About 5.5 mm. Stigma diameter: About 2 mm. Stigma shape: Club-shaped. Stigma color: Close to N79A. Style length: About 5.25 mm. Style color: Close to N80A. Ovary color: Close to 145A.

*Seeds and fruits.*—To date, seed and fruit development has not been observed on plants of the new *Veronica*.

Pathogen & pest resistance: To date, plants of the new *Veronica* have not been noted to be resistant to pathogens and pests common to *Veronica* plants.

Garden performance: Plants of the new *Veronica* have exhibited good garden performance and to be tolerant to rain, wind, high temperatures about 35° C. and to be suitable for USDA Hardiness Zones 4 through 9.

It is claimed:

1. A new and distinct *Veronica* plant named 'Allartist' as illustrated and described.

* * * * *